United States Patent [19]
Hicks et al.

[11] Patent Number: 6,156,703
[45] Date of Patent: Dec. 5, 2000

[54] METHOD OF INHIBITING FRUIT SET ON FRUIT PRODUCING PLANTS USING AN AQUEOUS EMULSION OF EICOSENYL EICOSENOATE AND DOCOSENYL EICOSENOATE

[75] Inventors: Scott C. Hicks; Sidney R. Siemer, both of Fresno; Don Barioni, El Centro; John Peterson, Fresno, all of Calif.

[73] Assignee: IJO Products, LLC, Fresno, Calif.

[21] Appl. No.: 09/316,483

[22] Filed: May 21, 1999

[51] Int. Cl.[7] .................................................. A01N 37/10
[52] U.S. Cl. ............................................................. 504/313
[58] Field of Search .................................... 504/116, 313

[56] References Cited

U.S. PATENT DOCUMENTS

| | | | |
|---|---|---|---|
| 4,613,359 | 9/1986 | Yamazaki et al. | 71/122 |
| 4,647,570 | 3/1987 | Shiokawa et al. | 514/341 |
| 4,742,060 | 5/1988 | Shiokawa et al. | 514/252 |
| 4,772,620 | 9/1988 | Shiokawa et al. | 514/341 |
| 4,774,247 | 9/1988 | Shiokawa et al. | 514/256 |
| 4,789,398 | 12/1988 | Yamazaki et al. | 71/122 |
| 4,803,277 | 2/1989 | Shiokawa et al. | 546/264 |
| 4,806,553 | 2/1989 | Shiokawa et al. | 514/332 |
| 4,812,454 | 3/1989 | Shiokawa et al. | 514/256 |
| 4,849,432 | 7/1989 | Shiokawa et al. | 514/341 |
| 4,914,113 | 4/1990 | Shiokawa et al. | 514/333 |
| 4,918,086 | 4/1990 | Gsell | 514/351 |
| 4,918,088 | 4/1990 | Gsell | 514/357 |
| 4,948,798 | 8/1990 | Gsell | 514/275 |
| 4,963,572 | 10/1990 | Gsell | 514/357 |
| 4,963,574 | 10/1990 | Bachmann et al. | 514/357 |
| 5,034,404 | 7/1991 | Uneme et al. | 514/365 |
| 5,034,524 | 7/1991 | Shiokawa et al. | 544/341 |
| 5,039,686 | 8/1991 | Davies et al. | 514/341 |
| 5,049,571 | 9/1991 | Gsell | 514/345 |
| 5,063,236 | 11/1991 | Gsell | 514/318 |
| 5,071,463 | 12/1991 | Narayanan et al. | 71/79 |
| 5,232,940 | 8/1993 | Hatton et al. | 514/407 |
| 5,236,938 | 8/1993 | Huang et al. | 514/341 |
| 5,242,891 | 9/1993 | Larsen et al. | 504/127 |

FOREIGN PATENT DOCUMENTS

| | | |
|---|---|---|
| 0135956 | 4/1985 | European Pat. Off. . |
| 0189972 | 8/1986 | European Pat. Off. . |
| 0192060 | 8/1986 | European Pat. Off. . |
| 0212600 | 3/1987 | European Pat. Off. . |
| 0235725 | 9/1987 | European Pat. Off. . |
| 0154178 | 10/1987 | European Pat. Off. . |
| 0254859 | 2/1988 | European Pat. Off. . |
| 0259738 | 3/1988 | European Pat. Off. . |
| 0295117 | 12/1988 | European Pat. Off. . |
| 0302389 | 2/1989 | European Pat. Off. . |
| 0302833 | 2/1989 | European Pat. Off. . |
| 0303570 | 2/1989 | European Pat. Off. . |
| 0306696 | 3/1989 | European Pat. Off. . |
| 0315826 | 5/1989 | European Pat. Off. . |
| 0163855 | 6/1989 | European Pat. Off. . |
| 0364844 | 4/1990 | European Pat. Off. . |
| 0375907 | 7/1990 | European Pat. Off. . |
| 0383091 | 8/1990 | European Pat. Off. . |
| 0385809 | 9/1990 | European Pat. Off. . |
| 0386565 | 9/1990 | European Pat. Off. . |
| 0403300 | 12/1990 | European Pat. Off. . |
| 0425978 | 5/1991 | European Pat. Off. . |
| 0428941 | 5/1991 | European Pat. Off. . |
| 0455000 | 11/1991 | European Pat. Off. . |
| 0464830 | 1/1992 | European Pat. Off. . |
| 0471372 | 2/1992 | European Pat. Off. . |
| 0679650 | 11/1995 | European Pat. Off. . |
| 3639877 | 5/1988 | Germany . |
| 3712307 | 10/1988 | Germany . |
| 19511269 | 10/1995 | Germany . |
| 52-005683 | 1/1977 | Japan . |
| 58-155354 | 3/1983 | Japan . |
| 63-287764 | 5/1987 | Japan . |
| 63-307857 | 6/1987 | Japan . |
| 2-207083 | 2/1989 | Japan . |
| 3-220176 | 1/1990 | Japan . |
| 3-246283 | 2/1990 | Japan . |
| 3-279359 | 3/1990 | Japan . |
| 3-255072 | 5/1990 | Japan . |
| 87/03781 | 7/1987 | WIPO . |
| 91/04965 | 4/1991 | WIPO . |
| 91/17659 | 11/1991 | WIPO . |
| 93/06089 | 4/1993 | WIPO . |
| 94/21606 | 9/1994 | WIPO . |
| 97/22593 | 6/1997 | WIPO . |

OTHER PUBLICATIONS

Committee on Jojoba Utilization, *Products From Jojoba: A Promising NewCrop for Arid Lands*, National Academy of Sciences, (1975).

Wisniak, Jamie, *Jojoba Oil and Derivatives*, Prog. Chem. Fats other Lipids, vol. 15, 167–218 (1977).

Tso, et al., *Inhibition of Tobacco Auxilary Bud Growth with Fatty Acid Methyl Esters*, J. Agr. Food Chem., 13(1): 78–81 (Jan.–Feb, 1965).

Sill et al., *Relationship Between Azalea Bud Morphology and Effectiveness of Methyl Decanoate, A Chemical Pinching Agent*, J. Amer. Soc. Hort. Sci. 95(3): 270–273 (1970).

Derwent WPI Acc No. 89–093657 (1989), abstract of BR 8803621 and patent family list.

Derwent WPI Acc No. 88–252222 (1988), abstract of FR 2611114 and patent family list.

*Primary Examiner*—Shelley A. Dodson
*Assistant Examiner*—Alton Pryor
*Attorney, Agent, or Firm*—Townsend and Townsend and Crew LLP

[57] ABSTRACT

A new fruit thinning agent comprising wax esters derived from esterification of monoethylenic acids and monoethylenic alcohols having between 18 and 24 carbons and a surfactant, or a combination of surfactants, said wax esters and surfactant at a concentration of between 1% v/v and 7% v/v of the total wax ester emulsion. Further, the invention provides a method of inhibiting fruit set for a fruit producing plant wherein the method comprises spraying an aqueous emulsion of a wax ester, or a mixture of wax esters, onto a fruit producing plant between the time of first bloom and the date of maximum fruit set, said emulsion in an amount to decrease fruit set by at least 10%.

14 Claims, No Drawings

METHOD OF INHIBITING FRUIT SET ON FRUIT PRODUCING PLANTS USING AN AQUEOUS EMULSION OF EICOSENYL EICOSENOATE AND DOCOSENYL EICOSENOATE

FIELD OF THE INVENTION

This invention relates to compositions of a fruit thinning agent comprising wax esters and a suitable surfactant, wherein the wax esters are the esterification product of monoethylenic acids and monoethylenic alcohols having between 18 to 24 carbons each. Methods of using the wax ester fruit thinning composition for horticultural treatment of fruit producing plants are also provided. Preferably, the wax esters composition is comprised of a mixture of wax esters which are at least 85% identical to the type and concentration of wax ester found in naturally occurring jojoba extract, with a surfactant, or combination of surfactants, at a concentration between 1% v/v and 10% v/v of the total wax ester composition.

BACKGROUND OF THE INVENTION

Over the last thirty years it has been a goal of various government agencies to develop uses for the desert plant jojoba (Simmondsia chinensis), especially the extract produced from the jojoba seeds. Due to the jojoba plant's ability to thrive in arid climatic conditions in coarse desert soils and it's life span which can extend up to 200 years, the plant was thought to be particularly useful for developing an agricultural industry in the underutilized lands of the American southwest.

The jojoba plant produces an abundance of seeds with an average yield for a mature plant of about 12 pounds (dry weight). Jojoba seeds contain about 50% by weight of a colorless, odorless oily extract which is commonly referred to as "jojoba oil". The extract is chemically an unsaturated wax made up of non-glyceride esters having a narrow range of chemical composition. Waxes of this type are relatively rare. Another natural source for wax esters is spermaceti, a wax produced from the head of the sperm whale. As the sperm whale is an endangered species and interstate sale of its oil was banned in 1973, it is not recognized as a particularly useful source for these wax esters.

Jojoba oil is more than 97% wax esters. Each wax ester is derived from one molecule of a long-chain monoethylenic alcohol esterified with one long-chain monoethylenic fatty acid. The wax esters typically are comprised of carbon chains of 38 to 44 carbon atoms. Suprisingly, the wax ester components of jojoba oil have been found to exhibit excellent flower thinning capabilities.

Fruit thinning is an advantageous and widely practiced procedure in the fruit crop industry. Many fruit bearing plants produce an excess of blossoms in a growing season. The excess flowers, and the eventual mature fruit, result in a small average fruit size and poor fruit quality for the fruit crop. Thus, in the grape industry it is desirable to reduce the number of berries on the rachis to permit larger berry size for market purposes. Further, an excess of fruit on a fruit bearing plant can result in a heavy load on the branches of the fruit tree, which reduces the tree's vigor and may lead to greater susceptibility to disease. Fruit thinning alleviates such problems and results in better a quality fruit crop.

Generally, fruit thinning entails the removal of a percentage of fruiting flowers or the prevention of formation of a percentage of fruiting bodies for a fruit bearing plant. Either the fruit producing blossoms or the immature fruit may be removed. Removal may be accomplished mechanically wherein workers will remove the fruiting flowers at some time prior to maturation. Alternatively, chemical means may be employed wherein a chemical, either in solution or powder form, is applied to the fruit trees at some optimum point before fruit maturation, thereby reducing the fruit load per fruit plant. Fruit thinning by chemical application is generally preferred as it is less labor intensive and thus less expensive.

Various chemical compounds have been disclosed which claim suitability for use as a fruit thinning agent. For example, U.S. Pat. No. 5,242,891 discloses the use of fatty acids, their salts and esters as a fruit thinning agent. The disclosed fatty acids generally have carbon chains of between 7 to 20 atoms. Additionally, U.S. Pat. No. 5,125,959 discloses pyrazole compounds for use as fruit thinning agents and U.S. Pat. No. 4,789,398 discloses the use of cholesterol as a fruit thinning agent. None of these application disclose the high molecular weight wax esters commonly found in jojoba extract for use as a flower thinning agent.

In addition to the fruit thinning ability of the wax esters found in jojoba extract, the wax esters have been found to exhibit other desirable qualities which make them a particularly effective fruit thinning agent. For example, the wax esters of jojoba extract are generally non-toxic for predator, beneficials and honeybees. The wax esters are also rainfast after the application has dried thoroughly. Thus, the wax esters are not easily washed off into the environment and fewer applications need be made relative to non-rainfast fruit thinning agents. As a result, environmental loading is kept to a minimum, costs are lowered for growers and the wax ester fruit thinning agent is environmentally safe. Additionally, the wax esters have been found to be non-phytotoxic and indeed, promote photosynthesis and stomatal conductance.

Another advantage of jojoba wax is the low volatility of wax esters. Many of the existing horticultural oils and fruit thinning agents are generally not environmentally safe in their application because they are somewhat volatile. Thus, use of these materials is hazardous to workers applying the chemical. The wax esters used in this invention provide particular stability and are significantly less volatile than horticultural oils. Specifically, the greater degree of unsaturation and the carbon chains, which are almost twice as long as fatty acid oils, enhances stability and non-volatility.

SUMMARY OF THE INVENTION

It has been discovered that wax esters having high molecular weight are a particularly effective and safe application for thinning fruit on orchard trees, plants and vines. This invention provides novel compositions of wax esters for horticultural treatment of plants comprising wax esters of between 36 to 44 carbon atoms and a surfactant or combination of surfactants. The wax esters are derived from the esterification of monoethylenic acids and monoethylenic alcohols having between 18 and 24 carbons and a surfactant, or combination of surfactants, at a concentration of between 1% v/v and 10% v/v of the total wax esters composition.

Additionally, the invention provides a method of inhibiting fruit set for a fruit producing plant wherein the method comprises spraying an aqueous emulsion of a wax esters with a surfactant or combination of surfactants onto the plant between the time of first bloom and the date of maximum fruit setting. The wax ester emulsion is applied in an amount to sufficient to decrease fruit setting by at least 10% of the amount in absence of the wax ester composition.

In a first aspect, the present invention provides a composition of wax esters with a surfactant, or a combination of surfactants. In a preferred embodiment, the wax ester composition comprises wax esters of between 36 to 44 carbon atoms and a surfactant or combination of surfactants necessary to emulsify the wax esters and impart uniform spreadability onto a flower surface.

In another preferred embodiment, the wax esters are derived from the esterification of monoethylenic acids and monoethylenic alcohols. The monoethylenic acids are chosen from a range of 18 to 22 length carbon chains and the monoethylenic alcohols from a range of 20 to 24 length carbon chains.

In another preferred embodiment of the present invention 50% to 90% of the wax esters is a mixture of eicosenyl eicosenoate and docosenyl eicosenoate.

In yet another preferred embodiment of the present invention, the wax esters are comprised of a mixture of wax esters which are 85% identical in type and concentration to the wax ester found in naturally occurring jojoba oil.

In yet another preferred embodiment of the present invention the fruit thinning agent is comprised of jojoba extract in an aqueous emulsion, with a suitable surfactant.

In a second aspect, the present invention provides a method of inhibiting fruit set on a fruit producing plant, the method comprising the spray application of an aqueous emulsion of a wax ester solution, the wax ester solution comprising a wax ester, or combination of wax esters with a surfactant, or combination of surfactants, onto a plant between the time of first bloom and the date of maximum fruit set wherein the wax ester emulsion is applied in an amount which would decrease fruit setting by at least 10% of the amount in absence of said wax ester emulsion.

In a preferred embodiment of the second aspect of the present invention, the wax esters are derived from the esterification of monoethylenic acids and monoethylenic alcohols. The monoethylenic acids are chosen from a range of 18 to 22 length carbon chains and the monoethylenic alcohols from a range of 20 to 24 length carbon chains.

In another preferred embodiment of the second aspect of the present invention, 50% to 90% of the wax esters are a mixture of eicosenyl eicosenoate and docosenyl eicosenoate.

In yet another preferred embodiment of the second aspect of the present invention, the wax esters are comprised of a mixture of wax esters which are 85% similar in type and concentration to the wax ester found in naturally occurring jojoba oil.

In yet another preferred embodiment of the second aspect of the present invention the fruit thinning agent is comprised of jojoba extract in an aqueous emulsion, with a suitable surfactant.

DEFINITIONS

The term "emulsion," as used herein refers to a stable mixture of two or more immiscible s held in suspension. The mixture may be stabilized by the presence of emulsifiers or surfactants.

The term "aqueous emulsion," as used herein refers to preparations of a liquid wax or oil distributed in small globules throughout the body of a second liquid which is water. When the dispersed liquid is an oil or wax and is in the discontinuous phase and the dispersion medium is in the continuous phase it is an oil in water emulsion, whereas when water or aqueous solution is the dispersed phase and oil, wax or is the continuous phase, it is known as a water in oil emulsion.

The term "surfactants," as used herein refers to emulsifiers, detergents, surface active agents, anti-foaming agents or compounds which reduce surface tension when dissolved in water of a water solution, or which reduce interfacial tensions between two liquids. Thus the surfactant changes the properties of a solvent so that immiscible liquids may be more easily stabilized. Fundamentally, a surfactant is a single molecule comprised of two structurally dissimilar groups of opposing solubility tendencies, one which has an affinity for the phase and the other which is antipathic to the medium. The surfactant causes adsorption at the solution's interfaces, orientates the adsorbed surfactant ions or molecules, promotes micelle formation in the bulk of the solution, and orientates the surfactant ions or molecules in the micelle, thereby increasing the solubility of the solvent and stabilizing the mixture.

The term "wax esters," as used herein refers to esters of long chain, even-numbered fatty acids and monohydric, straight chain, aliphatic alcohols, or sterols. Waxes are usually ester mixtures often accompanied by small percentages of free fatty acids or high molecular weight unbranched hydrocarbons. The wax acids and wax alcohols usually have a similar number of carbon atoms and are very hydrophobic.

The term "monoethylenic acids," as referred herein refers to carboxylic acid organic compounds where the carboxyl group is attached to one end of a hydrocarbon and the hydrocarbon contains a single double bond.

The term "monoethylenic alcohols," as referred herein refers to organic compounds where one or more hydroxyl groups (OH) are present in a hydrocarbon molecule with no more than one hydroxyl group attached to a single carbon atom and which also includes a single double bond in the hydrocarbon molecule.

The term "non-ionic surfactants," as referred to herein refers to surfactants, detergents or emulsifiers which do not ionize in water and thus are not subject to hydrolysis by aqueous solutions of acid or alkali.

The term "siloxanes," as referred to herein refers to straight chain compounds consisting of silicon atoms single-bonded to oxygen and arranged so that each silicon atom is linked with four oxygen atoms. In some cases, hydrogen may replace two or more of the oxygens.

The term "polysiloxanes," as referred herein refers to siloxane chains wherein some of the oxygens are replaced with organic substituents so that a linear polymer results.

DETAILED DESCRIPTION

Introduction

The ability to control fruit yield for a fruit or vegetable producing plant such as grape vines, plums and tomatoes is important for producing a high quality fruit or vegatable crops. Fruit thinning, by application of a fruit or flower thinning chemical agent is a popular approach to improving fruit quality and maintaining healthy orchard plants. A variety of chemicals have been explored in this context.

It has recently been found that long chain wax esters have special utility as a fruit thinning agent. Particularly, aqueous emulsions of liquid wax esters with a suitable surfactant, wherein the wax esters are the esterification product of monoethylenic acids of between 18 and 22 carbon chains and monoethylenic alcohols of between 20 to 24 carbon chains, are useful as fruit thinning agent. This invention provides compositions and methods of use for wax ester fruit thinning agents.

Wax Ester Sources

The wax esters of this invention are most conveniently extracted from *Simmondsia chinensis* (Jojoba). *S. Chinensis* is grown commercially for its wax esters. However, this invention is not intended to be limited by the origin of the wax esters of either synthetically or biologically origin. Sexual crosses between species is the genus. Related species in the genus are expected to yield novel plants which produce the wax esters for use in this invention.

Jojoba extract is more than 97% wax esters. Wax esters are derived from one molecule of a long-chain alcohol esterified with one long-chain fatty acid. Jojoba oil contains no glycerides, very little (1 percent) free acid or alcohol, and almost no hydrocarbons, steroids or other contaminants. Carbon chains of 18 and 24 atoms long make up about 93% of the acids and alcohols in the wax esters.

The unsaturated acid components of jojoba's wax esters are mostly a mixture of eicosanoic ($C_{20}$), docosanoic ($C_{22}$) and octadecanoic ($C_{18}$) acids. The unsaturated alcohols are a mixture of eicosanol and docosanol, with smaller quantities of tetracosanol ($C_{24}$) and alcohols of lower molecular weight. Over 85% of the esters present in jojoba oil are combinations of $C_{20}$ and $C_{22}$ acids and alcohols. The double bond position on the acids and alcohols typically falls between carbon 11 and carbon 12, and between carbon 13 and carbon 14.

More accurately, the alcohol content is comprised of 43.8% Eicos-11-enol, 44.9% Docos-13 enol and 8.9% Tetracos-15-enol ($C_{24}$). The acid content consists of 71.3% Eicos-11-enoic acid, 13.6% Docos-13-enoic acid and 10.1% Octdec-9-enoic acid. Percentage's of composition components at or below 2% are defined as trace components and are not included in this description.

Further, the wax esters present in jojoba oil typically break down to 30.9% Eicosenyl Eicosenoate ($C_{40}$), 43.2% Docosenyl Eicosenoate ($C_{42}$), 7.6% Eicosenyl Docosenoate ($C_{42}$), 6.2% Tetracosenyl Eicosenoate ($C_{44}$) and 5.9% Eicosenyl Octadecenoate ($C_{38}$). Percentage's of components below 2% were defined as trace components and not included in the above description.

Extraction of Wax Esters from Natural Sources

The extraction of wax esters from jojoba can be carried out by any standard technique as is used in the industry for the extraction of fats or waxes from seeds, beans or nuts. For example, crushing or pressing the seeds and collecting the wax is one such technique. Other techniques contemplated may be the use of solvents to extract the wax. Solvents such as benzene, hexane, heptane and carbon tetrachloride have been shown to readily extract the desired wax esters in a satisfactory yield without special difficulty or affecting properties of the wax esters.

Synthesis of Wax Esters

Although it is preferable to extract the wax esters for the subject invention from naturally occurring sources such as jojoba plant, esters of this invention can be synthesized by a variety of standard esterification methods as is known in the art (see March, J., "Advanced Organic Chemistry—Reactions, Mechanisms, and Structures", $4^{th}$ ed., (1992)). For example, an acid catalyzed esterification of carboxylic acids with alcohols (the Fischer esterification reaction), wherein equilibrium is driven to the right, is one such esterification technique. Techniques commonly used to drive this reaction to the right include adding an excess of reactant (usually the alcohol), removal of the ester or water product by distillation, or removal of the water product by azeotropic distillation, use of a dehydrating agent or a molecular sieve.

One skilled in the art would appreciate that this is just one of several esterification reactions available to the synthesize the wax esters contemplated in this invention.

As described above, the esterification reactions would be carried out with monoethylenic acids and alcohol precursors comprising carbon chains from about 18 to 24 carbon atoms, which are commonly sold by a variety of vendors. For the purposes of illustration, purchasing 13-docosaenoic acid and 11-eicosenol from Sigma-Aldrich Fine Chemicals Co. (see Sigma Catalog for Biochemicals and Reagents for Life Sciences, pg. 417 and 407 respectively, (1999)), combining these two precursors with an acid catalyst such as $H_2SO_4$ or TsOH while drawing off the product ester or water by distillation would give the wax ester docosenol eicosenoate, a wax ester whose use as a fruit thinning agent is detailed in this invention.

Application of Wax Ester Fruit Thinning Agents

The wax ester fruit thinning composition may be applied to a variety of fruit bearing plants including trees, bushes or vines. Specifically, the subject invention is contemplated to be used on grape vines, apple, plum, pear or peach trees, or vegetable plants where fruit flowers form and fruit matures above ground, such as eggplant and tomatoes. Other species of fruit or vegetable producing plants which may be thinned by the subject invention would be obvious to any person skilled in the art.

The wax ester fruit thinning composition according to this invention may be formulated into various forms such as solution, wettable powder, emulsion or spray, by mixing with any suitable solid or liquid carrier such as water. It is preferred that the wax esters and surfactant composition is applied in the form of an aqueous emulsion.

The wax ester formulation may be applied by any of the methods typically known and used in the agricultural industry for the application of a chemical. Preferably, the wax ester composition would be applied by any common spraying technique, including crop dusting by airplane or vehicle. However, the most preferable method for application of the subject wax ester fruit thinning agent is by any ground or hand sprayer which is commonly used in the agricultural industry. Optimally, the wax ester emulsion is sprayed over the entire plant just to the point of runoff.

The surfactants which can be employed in the wax ester composition can be any of the non-phytotoxic surfactants which are customarily used in preparing agricultural formulations. The surfactant would be one which adequately increases the solubility of the wax ester in water and which stabilizes the mixture by increasing break time so that the wax ester emulsion stays in the emulsified state long enough to be applied over a large acreage. Further, a surfactant should be chosen which increase the spreadability of the wax ester composition, so that the wax ester solution spreads at the same rate as the water phase over the fruiting flower. In this way a filmy, uniform application of the wax esters is achieved. Specifically, it is preferred for the present invention that the wax esters be mixed with a non-ionic surfactant, a siloxane or a polysiloxane. Surprisingly, it was found that the optimal composition was one where the wax esters were mixed with a non-ionic detergent to increase solution stability and then with a polysilane to enhance spreadability. Thus, the most preferred composition is one in which a combination of surfactants are employed. These type of surfactants and their use are well known in the art. A preferable non-ionizable surfactant would be IGEPAL CO [nonylphenoxypoly(ethyleneoxy)ethanol] or IGEPAL CA [octyphenoxypoly(ethyleneoxy)ethanol], manufactured by Rhone-Poulenc. Additionally, a preferable polysilane surfactants would be a polyether-polymethylsiloxane-copolymer such as Break-Thru® OE 441, a polysiloxane manufactured by Goldschmidt Chemical Corporation.

The wax ester composition of the present invention can be diluted in order to facilitate its application in the field. Preferably, the wax ester/surfactant mixture would be diluted in water to form an aqueous emulsion and sprayed over the plant. The dilution should be at a concentration to maximize flower thinning activities without injuring the plant. It is preferred that the wax ester composition be diluted from 0.25% v/v to about 10% v/v in water for optimum flower thinning activity. For example, a 2% to 4% emulsion would be produced by mixing 1–2 pints of the wax ester/surfactant composition with approximately 40 to 50 gallons of water, for treatment of approximately one acre of orchard trees. One skilled in the art would appreciate that the stated volume of wax ester fruit thinning agent for treatment of one acre represents an application for intermediate foliage. The volume would be increased when the foliage of the treated plants is mature and abundant, and decreased when the foliage is relatively new and sparse.

In addition to large scale applications for farms, greenhouse and agribusiness crop lands, the wax ester fungicidal agent can be employed as a fruit thinning agent for home and garden plants. Thus, it is contemplated that the wax ester agent is also used in a ready-to-use formulation for home use. The preferred concentrations of wax ester to surfactant to water is consistent as to what has been described herein. Preferably, the ready-to-use formulation would be 5% wax ester, 3.5% non-ionic surfactant and 3.5% siloxane or polysiloxane surfactant, all of which is diluted in water to form an 12% wax ester/surfactant concentration in water. In addition, a non-diluted wax ester/surfactant preparation of the same proportions above may be formulated as a refill product, where the refill product will later be diluted at the home by approximately 1 ounce of wax ester/surfactant to 1 quart of water.

Those skilled in the art will appreciate that the optimum time of application is determined by the particular fruiting characteristics of the subject plant species. Generally, the optimum time to apply the wax ester composition can be at any time between first bloom and the date of maximum fruit set. More particularly, the subject wax ester fruit thinning agent should be applied at approximately 20% to 80% of maximum bloom for about 80% of the pants to be treated. Optimally, the wax ester fruit thinning agent should be applied at approximately 40% to 60% of maximum bloom for about 90% of the plants to be treated. For example, the optimum date of application of a wax ester emulsion for Flame seedless grape vines, would be at 50% of maximum bloom.

While a single application of the wax ester fruit thinning agent should be satisfactory for effective fruit thinning, the wax ester fruit thinning agent may be applied multiple times to achieve the desired fruit thinning effect. However, in applications wherein the wax ester composition make up more than 2.5% of the aqueous solution by volume, a subsequent application made within 10 days may cause some foliage injury depending on the plant species.

EXAMPLES

The following examples are offered to illustrate, but not to limit the claimed invention.

Example 1 details a wax ester fruit thinning formulations.

Example 2 illustrates the application of wax esters as a fruit thinning agent on grape vines.

Example 3 illustrates the fruit thinning ability of aqueous emulsions wax esters by their application on plum trees.

Example 1

Example 1 provides a preparation of a wax ester and surfactant composition diluted water to form an aqueous emulsion for use as a fruit thinning agent. Specifically, herein is provided the preparation of a composition of wax esters which resemble in type and concentration the wax esters found in jojoba extract by at least 85%, with a combination of surfactants to increase stability and spreadability of the wax ester solution, in an aqueous emulsion.

Formulation

A solution containing 93% v/v of a wax ester mixture comprising 43% docosenyl ecosenoate, 30% eicosenyl eicosenoate, 7.5% eicosenyl eicosenoate, 6% tetracosenyl eicosenoate and 5% eicosenyl octadecenoate, with a 7% mixture of surfactants was prepared. The solution was prepared by mixing together 93% jojoba extract v/v with 3% v/v a non-ionic type surfactant and 4% polysiloxane type surfactant. The non-ionic surfactant was Igepal CA-520 from Rhone-Poulenc, which is an octylphenol ethoxylate containing 5 moles by weight of ethylene oxide. The polysiloxane used was Break-Thru® OE-441 from Goldschmidt Chemical Corporation, which is a polyether-polymethylsiloxane-copolymer. The wax ester and surfactant composition was mixed for 20 minutes by return flow agitation. The resultant solution contained the wax esters at the desired stability and spreadability to effectively treat the fruiting flower surface. The wax ester solution can then be diluted in water to form an aqueous emulsion for application to a fruit bearing tree.

Stability

The stability of a wax ester aqueous emulsion was tested by observing wax ester/surfactant compositions of 3% v/v, 5% v/v and 7% v/v octyphenol ethoxylate in jojoba extract. A 5% wax ester emulsion was prepared by diluting 5 ml of the wax ester composition in 95 ml of water. Observations of the time period before emulsion break of the wax ester emulsions were made. It was found that higher concentrations of surfactant produced a longer time period before emulsion break as well as less free wax ester formation. Further, an emulsion without any surfactant produced a solution of primarily two phases with little observed emulsification of the wax esters.

The spreadability of the wax ester/surfactant solution in which the surfactant consisted of a non-ionic detergent was found to be adequate, but not optimal. The addition of a polysiloxane surfactant proved to enhance the spreadabiltiy of the wax ester composition. Thus, the particular utility of a non-ionic surfactant and a polysiloxane was illustrated by application of an aqueous emulsion of wax esters to the leaf surfaces of Escalonia plant. The plants were treated with a wax ester/surfactant composition of 3% v/v octylphenol ethoxylate, 4% polyether-polymethylsiloxane-copolymer and 93% jojoba extract. A 1% aqueous emulsion was prepared by diluting 5 ml of the wax ester solution in 495 ml of water. It was observed that the oil and water phases for the wax ester aqueous emulsions spread at a fairly uniform rate, with the fronts of both phases moving at approximately the same rate. Further, upon evaporation of the water phase, it was observed that the wax esters had spread uniformly over the surface of the plant leaf. That is, globules of wax ester were not observed but rather the wax ester composition formed a filmy, uniform deposit on the Escalonia leaf.

Example 2

Example 2 details the application of a wax ester and surfactant composition in an aqueous emulsion on grape vines and illustrates its utility as a fruit thinning agent.

The wax ester and surfactant fruit thinning agent was prepared according to Example 1 and diluted in water by mixing 1 ml wax ester composition to 99 ml water to form a 1% aqueous emulsion The wax ester emulsion was applied to 40 plants with more than 100 individual grape bunches of the Flame seedless variety. The wax ester fruit thinning agent was applied at approximately 40% of full bloom for 90% of the grape bunches by a hand sprayer, just to the point of runoff, and was applied over the entire surface of the grape vines. A second application of the same composition and dilution was made 4 days later, at approximately 60% of full bloom.

The grape plants were evaluated for berry formation 2 months after the first application. The data was evaluated by comparing the amount of average berry formation per plant with that of untreated grape plants of the same variety, maturity and location. It was found that the wax ester treated plants exhibited a 20% reduction in berry formation versus that of the untreated plants. Further, the treated plants produced a larger average berry size and the grape plant appeared more vigorous than untreated grape plants.

Example 3

Example 3 demonstrates an aqueous emulsion of wax esters application for inhibiting fruit set on plum trees.

The wax ester fruit thinning agent was prepared according to Example 1 at concentrations of 1%, 2.5% and 5% (by volume) diluted in water. The wax ester emulsion was applied onto separate trees of the Friar plum tree variety. Carnuba wax was applied to a separate tree for comparative purposes and both the wax ester emulsion and a carnuba wax emulsion were compared to untreated trees to establish the fruit thinning capability of the wax esters. The wax ester and carnuba wax were applied to trees comprising 10–30 branches wherein each branch consisted of 50 to 200 blossoms. The wax ester was applied by handsprayer to runoff on Mar. 2, 1999, at which the plants exhibited bloomage of 40% to 60% of full bloom.

Data was gathered at intervals of 14, 20, 27 and 34 days after application. On those days, evaluation consisted of counting flowers and/or fruitlets until fruit drop stabilized in the untreated pots. Table 1 summarizes the percentage flower reduction data for the unsaturated wax ester treatment, carnuba wax treatment and untreated plants.

TABLE 1

Percentage Flower Reduction for Friar Variety Plum Trees

| Formulation/Time (days) | 14 | 20 | 27 | 34 |
|---|---|---|---|---|
| Untreated | 0.0% | 18.5% | 29.0% | 40.5% |
| 1% Wax Ester | 1.5% | 14.5% | 45.5% | 51.0% |
| 2.5% Wax Ester | 24.0% | 58.0% | 60.5% | 77.0% |
| 5% Wax Ester | 21.0% | 64.5% | 74.5% | 80.5% |
| 2.5% Wax Esters and .05% Surfactant | 33.5% | 57.0% | 64.0% | 73.5% |
| Carnuba Wax | 22.0% | 50.5% | 66.0% | 69.0% |

It was found that a wax ester solution effectively thins plum trees, with as much as twice the percentage of flower reduction than that of non-treated trees. Further, the treated plum trees produced a larger average fruit size than the untreated plum trees.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of inhibiting fruit setting on a fruit producing plant, said method comprising:

spraying an aqueous emulsion of a wax ester, or mixture of wax esters, onto the plant between the time of first bloom and the date of maximum fruit setting, said emulsion in an amount to decrease fruit setting by at least 10% of the amount in absence of said ester and wherein at least 50% of the wax ester is an esterification product of monoethylenic acids and monoethylenic alcohols having 18 and 22 carbons.

2. The method of claim 1 wherein the plant is a grapevine.

3. The method of claim 1 wherein the plant is an orchard fruit tree.

4. The method of claim 1 wherein the plant is selected from the group comprising: an apple tree, a peach tree, a nectarine tree, a plum tree, an orange tree or a grapefruit tree.

5. The method of claim 1 wherein the wax ester is jojoba oil.

6. The method of claim 1 wherein the emulsion further comprises a surfactant.

7. The method of claim 1 wherein the emulsion further comprises a surfactant selected from a group consisting of non-ionic detergents.

8. The method of claim 1 wherein the emulsion further comprises a surfactant selected from a group consisting of: ethoxylated alkyl phenyl ethers, siloxanes and polysiloxanes.

9. The method of claim 6 wherein the weight ratio of surfactant to wax esters is from 1:10 to about 1:50.

10. The method of claim 1 wherein the emulsion further comprises a combination of two surfactants.

11. The method of claim 10 wherein the emulsion comprises a combination of surfactants selected from a group consisting of ethoxylated alkyl phenyl ethers, siloxanes and polysiloxanes and are not the same.

12. The method of claim 10 wherein the combination of surfactants is at a ratio of 1:1 to about 1:4 by weight to each other.

13. The method of claim 1 wherein the emulsion is between about 0.25% and about 7% v/v wax esters.

14. The method of claim 1 wherein about 50% to about 90% of the wax ester is a mixture of ecosenyl eicosenoate and decosenyl eicosenoate.

* * * * *